(12) United States Patent
Green et al.

(10) Patent No.: US 6,605,622 B2
(45) Date of Patent: Aug. 12, 2003

(54) USE OF ANTI-ESTROGENIC COMPOUNDS AS ANTI-FUNGAL AGENTS

(75) Inventors: Shawn J. Green, Vienna, VA (US); Adonia Papathanassiu, Silver Springs, MD (US)

(73) Assignee: EntreMed, Inc., Rockville, MD (US)

( * ) Notice: Subject to any disclaimer, the term of this patent is extended or adjusted under 35 U.S.C. 154(b) by 0 days.

(21) Appl. No.: 09/866,279

(22) Filed: May 25, 2001

(65) Prior Publication Data

US 2001/0044432 A1 Nov. 22, 2001

Related U.S. Application Data

(63) Continuation of application No. 09/371,585, filed on Aug. 10, 1999, now Pat. No. 6,239,123.
(60) Provisional application No. 60/096,145, filed on Aug. 11, 1998.

(51) Int. Cl.[7] ............................................. A61K 31/445
(52) U.S. Cl. ..................................................... 514/324
(58) Field of Search ......................................... 514/324

(56) References Cited

U.S. PATENT DOCUMENTS

| | | |
|---|---|---|
| 2,584,271 A | 2/1952 | Huffman |
| 2,846,453 A | 8/1958 | Hoehn |
| 3,410,879 A | 11/1968 | Smith et al. |
| 3,470,218 A | 9/1969 | Farah |
| 3,492,321 A | 1/1970 | Crabbe |
| 3,496,272 A | 2/1970 | Kruger |
| 3,956,348 A | 5/1976 | Hilscher |
| 4,172,132 A | 10/1979 | Draper et al. |
| 4,212,864 A | 7/1980 | Tax |
| 4,307,086 A | 12/1981 | Tax |
| 4,522,758 A | 6/1985 | Ward et al. |
| 4,743,597 A | 5/1988 | Javitt et al. |
| 4,994,443 A | 2/1991 | Folkman et al. |
| 5,001,116 A | 3/1991 | Folkman et al. |
| 5,135,919 A | 8/1992 | Folkman et al. |
| 5,504,074 A | 4/1996 | D'Amato et al. |
| 5,521,168 A | 5/1996 | Clark |
| 5,621,124 A | 4/1997 | Seilz et al. |
| 5,643,900 A | 7/1997 | Fotsis et al. |
| 5,661,143 A | 8/1997 | D'Amato et al. |

(List continued on next page.)

FOREIGN PATENT DOCUMENTS

| | | |
|---|---|---|
| DE | 1907330 | 10/1969 |
| DE | 3625315 | 1/1998 |
| WO | WO 90/15816 A1 | 12/1990 |
| WO | WO 93/03729 | 3/1993 |
| WO | WO 93/19746 | * 10/1993 |
| WO | WO 95/04535 | 2/1995 |
| WO | WO 98/40398 | 9/1998 |

OTHER PUBLICATIONS

Beggs, William H. "Anti–candida activity of the anti–cancer drug tamoxifen." Research Communications in Chemical Pathology and Pharmacology, (1993) Vol 80, No. 1, pp. 125–128 ISSN: 0034–5164.*

Title: Lilopristone/(1–[4–(Dimethylamino)phenyl]–17–hydroxy–17–(3–hydroxy–1–propenyl)estra–4,9–diene–3–one; AK 98734 Publ: *Dict. of Drugs (1990), Dict. of Steroids (1991), Dict. of Org. Cmpds (6th Ed) (1996), Dict. of Pharm. Agents (1997).*

Title: (paragraphs 583–584) Publ: *The Merck Index 11th Edition* pp.: 88 Date: 1989.

(List continued on next page.)

Primary Examiner—Theodore J. Criares
Assistant Examiner—Jennifer Kim
(74) Attorney, Agent, or Firm—Kilpatrick Stockton LLP

(57) ABSTRACT

The present invention provides compounds that are useful for inhibiting the proliferation of fungi. The compounds are estrogenic derivatives, such as 2ME2, or anti-estrogenic compounds. The compounds may be used for treating infections of fungi in humans and animals, or to prevent or inhibit the growth of fungi on any surface.

8 Claims, 1 Drawing Sheet

U.S. PATENT DOCUMENTS

| | | | |
|---|---|---|---|
| 5,892,069 A | 4/1999 | D'Amato et al. | |
| 6,011,023 A | 1/2000 | Clark et al. | |
| 6,136,992 A | 10/2000 | Ram et al. | |
| 6,200,966 B1 | 3/2001 | Stewart | |
| 6,239,123 B1 | 5/2001 | Green et al. | |
| 6,399,773 B1 * | 6/2002 | Liu et al. ................... | 544/106 |

OTHER PUBLICATIONS

Author: Adams, E.F. et al. Title: Steroidal regulation of oesteradiol–17B dehydrogenase activity of the human breast cancer cell line MCF–7 Publ: *Journal of Endrocrinology* Vol/Iss: 188 (1) pp.: 149–154 Date: Jul. 1988.

Author: Aizu–Yokota et al. Title: Natural Estrogens Induce Modulation of Microtubules in Chinese Hamster V79 Cells in Culture Publ: *Cancer Research* Vol/Iss: 55 pp.: 1863–1868 Date: May 1, 1995.

Author: Attalia et al. Title: 2–Methoxyestradiol Arrests Cells in Mitosis without Depolarizing Tubulin Publ: *Biochemical and Biophysical Research Communications* Vol/Iss: 228 pp.: 467–473 Date: 1996.

Author: Ayala et al. Title: The Induction of Accelerated Thymic Programmed Cell Death During Polymicrobial Sepsis: Control by Corticosteroids but not Tumor Necrosis Factor (Abstract only) Publ: *Shock* Vol/Iss: 3 (4) pp.: 259–267 Date: Apr. 1995.

Author Banik et al. Title: Orally Active Long–Acting Estrogen (3–(2–propynyloxy)–estra–1,3,5,(10)–triene–17. beta.–ol trimethylacetate) (Identifier only) Publ: *Steroids* Vol/Iss: 16 (3) pp.: 289–296 Date: 1970.

Author: Bardon et al. Title: Steroid Receptor–Mediated Cytotoxicity of an Antiestrogen and an Antiprogestin in Breast Cancer Cells (Abstract only) Publ: *Cancer Research* Vol/Iss: 47 (5) pp.: 1441–1448 Date: Mar. 1, 1987.

Author: Bhat et al. Title: Estradiol–induced Mitotic Inhibition in the Bursa of Fabricius of Male Domestic Duckling Publ: *Mikroskopie* Vol/Iss: 39 pp.: 113–117 Date: May 1982.

Author: Blagosklonny et al. Title: Raf–1/bcl–2 Phosphorylation: A Step from Microtubule Damage to Cell Death Publ: *Cancer Research* Vol/Iss: 57 pp.: 130–135 Date: Jan. 1, 1997.

Author: Blickenstaff et al. Title: Estrogen–Catharanthus (Vinca) Alkalid Conjugates Publ: *Cytotoxic Estrogens in Hormone Receptive Tumors* pp.:89–105 Date: 1980.

Author: Boye et al. Title: 185. Deaminocolchinyl Methyl Ether: Synthesis from 2,3,4,4'–Tetramethoxybiphenyl–2–carbaldehyde. Comparison of Antitubulin Effects of Publ: *Helvetica Chimica Acta* Vol/Iss: 72 pp.: 1690–1696 Date: 1989.

Author Brodie, A.M. Title: Aromatase Inhibitors in the Treatment of Breast Cancer (Abstract only) Publ: *Journal of Steroid Biochemistry and Molecular Biology* Vol/Iss: 49 (4–6) pp.:281–287 Date: Jun. 1994.

Author: Brosens et al. Title: Comparative Study of the Estrogenic Effect of Ethinylestradiol and Mestranol on the Endometrium Publ: *Laboratory for Gynecological Physiopathology* Vol/Iss: 14 (6) pp.: 679–685 Date: Dec. 1, 1976.

Author: Castagnetta, L. et al. Title: Simple Approach to Measure Metabolic Pathways of Steroids in Living Cells Publ: *Journal of Chromatography* Vol/Iss: 572 pp.: 25–39 Date: Dec. 6, 1991.

Author: Chasserot–Golaz et al. Title: Biotransformation of 17.beta–hydroxy–11.beta.–(4–dimethylaminophenyl) 17.alpha.1–propynyl–estra–4,9–diene–3–one (RU486) in Rat Hepatoma Variants (Identifier only) Publ: *Biochemical Pharmacology* Vol/Iss: 46 (11) pp.: 2100–2103 Date: Jan. 1, 1993.

Author: Chen et al. Title: A New Synthetic Route to 2–and 4–Methoxyestradiols by Nucleophilic Substitution Publ: *Steroids* Vol/Iss: 47 (1) pp.: 63–66 Date: Jan. 1986.

Author: Chen et al. Title: Synthesis of 11.beta.–(4–dimethylaminophenyl)–17.beta–hydroxy–17. alpha.–(1–propyl) estra–4,9–dien–3–one (RU486) (Identifier only) Publ: *Nanjing Yaoxueyuan Xuebao* Vol/Iss: 17 (4) pp.: 282–285 Date: 1986.

Author: Cohen et al. Title: Novel Total Synthesis of (+)–Estrone 3–Methyl Ether, (+)–13B–Ethyl–3–methoxygona–1,3, 5(10–triene–17–one, and (+)–Equilenin 3–Methyl Ether Publ: *The Journal of Organic Chemistry* Vol/Iss: 6 pp.: 681–685 Date: Mar. 21, 1975.

Author: Collins et al. Title: The Structure and Function of Estrogens. XI* Synthesis of (±)–7(8–11α) abeo–Estradiol and its 9,11–Didehydro Derivative Publ: *Aust. Journal of Chemistry* Vol/Iss: 45 pp.: 71–97 Date: 1992.

Author: Crum, R. et al. Title: A New Class of Steroids Inhibits Angiogenesis in the Presence of Heparin or a Heparin Fragment Publ: *SCIENCE* Vol/Iss: 230 pp.: 1375–1378 Date: Dec. 20, 1985.

Author: Cummings et al. Title: Apoptosis Publ: *The American Journal of Surgical Pathology* Vol/Iss: 21 (1) pp.: 88–101 Date: 1997.

Author: Cushman et al. Title: Synthesis, Antitubulin and Antimitotic Activity, and Cytotoxicity of Analogs of 2–Methoxyestradiol, an Endogenous Mammalian Metabolite of Estradiol that Publ: *Journal of Medical Chemistry* Vol/Iss: 38 (12) pp.: 2041–2049 Date: 1995.

Author: Cushman et al. Title: Synthesis of Analogs of 2–Methoxyestradiol with Enhanced Inhibitory Effects of Tubulin Polymerization and Cancer Cell Growth Publ: *Journal of Medical Chemistry* Vol/Iss: 40 (15) pp.: 2323–2334 Date: 1997.

Author: D'Amato et al. Title: 2–Methoxyestradiol, an Endogenous Mammalian Metabolite, Inhibits Tubulin Polymerization by Interacting at the Colchicine Site Publ: *Proceedings of the National Academy of Science USA* Vol/Iss: 91 pp.: 3964–3968 Date: Apr. 1994.

Author: Dvir et al., Title: Thin–layer Chromatography of DANSYL–oestrogens Publ: *Journal of Chromatography* Vol/Iss: 52 pp.: 505–506 Date: Nov. 4, 1970.

Author: Epe et al. Title: Microtubular Proteins as Cellular Targets for Carcinogenic Estrogens and Other Carcinogens Publ: *Mechanisms of Chromosome Distribution and Aneuploidy* pp.: 345–351 Date: 1989.

Author: Evans et al. Title: A Convergent Total Synthesis of (30 )–Colchicine and (+)–Desacetamidoisocolchicine Publ: *Journal of American Chemistry Society* Vol/Iss: 103 pp.: 5813–5821 Date: Sep. 23, 1981.

Author: Fishman, J. Title: Synthesis of 2–Methoxyestrogens Publ: *Journal of the American Chemical Society* Vol/Iss: 80 pp.: 1213–1216 Date: Mar. 5, 1998.

Author: Fitzgerald Title: Molecular Features of Colchicine Associated with Antimitotic Activity and Inhibition of Tubulin Polymerization Publ: *Biochemical Pharmacology* Vol/Iss: 25 pp.: 1383–1387 Date: Jun. 15, 1976.

Author: Fotsis et al. Title: The Endogenous Oestrogen Metabolite 2–Methoxyoestradiol Inhibits Angiogenesis and Suppresses Tumour Growth Publ: *Nature* Vol/Iss: 368, pp.: 237–239 Date: Mar. 17, 1994.

Author: Getahun et al. Title: Synthesis of Alkoxy–Substituted Diaryl Compounds and Correlation of Ring Separation with Inhibition of Tubulin Polymerization: Differential Enhancement of Inhibitory Effects Under Suboptimal Polymerization Publ: *Journal of Mecial Chemistry* Vol/Iss: 35 (6) pp.: 1058–1067 Date: Mar. 20, 1992.

Author: Gross et al. Title: Inhibition of Tumor Growth, Vascularization, and Collagenolysis in the Rabbit Cornea by Medroxyprogesterone, Publ: *Procedings of the National Academy of Science USA* Vol/Iss: 78 (2), pp.: 1176–1180 Date: Feb. 1981.

Author: Guangrong et al. Title: Effect of Components of Crowth Ether Copper(I)Iodide Mixed Catalyst on Nucleophilic Substitution of Bromoestrogen (Abstract No. 195225) Publ: *Chemical Abstracts* Vol/Iss: 111 (21) pp.: 818, Column 1 Date: Nov. 20, 1989.

Author: Haldar et al. Title: Bcl2 is the Guardian of Microtubule Integrity Publ: *Cancer Research* Vol/Iss: 57 pp.: 229–233 Date: Jan. 15, 1997.

Author: Hamel et al. Title: Interactions of 2–Methoxyestradiol, an Endogenous Mammalian Metabolite, with Unpolymerized Tubulin and with Tubulin Polymers Publ: *Biochemistry* Vol/Iss: 35 (4) pp.: 1304–1310 Date: 1996.

Author: Hartley–Asp et al. Title: Diethylstilbestrol Induces Metaphase Arrest and Inhibits Mcirotubule Assembly Publ: *Mutation Research* Vol/Iss: 143 (4) pp.: 231–235 Date: Aug. 1985.

Author: He et al. Title: A Versatile Synthesis of 2–Methoxyestradiol, an Endogenous Metabolite of Estradiol which Inhibits Tubulin Polymerization by Binding to the Colchicine Biding Site Publ: *Biiorganic & Medicinal Chemistry Letters* Vol/Iss: 4 (14) pp.: 1724–1728 Date: 1994.

Author: Huber et al. Title: Tubulin Binding of Conformationally Restricted Bis–Aryl Compounds Publ: *Bioorganic & Medicinal Chemistry Letters* Vol/Iss: 1 (5) pp.: 243–246 Date: 1991.

Author: Josefsson et al. Title: Supression of Type II Collagen–Induced Arthritis by the Endogenous Estrogen Metabolite 2–Methoxyestradiol Publ: *Arthritis & Rheumatism* Vol/Iss: 40 (1) pp.: 154–163 Date: Jan. 1997.

Author: Kabarity et al. Title: Further Investigations of the cytological effects of some contraceptives Publ: *Mutation Research* Vol/Iss: 135 pp.: 181–188 Date: 1984.

Author: Kelly et al. Title: The Stimulation of Prostaglandin Production by Two Antiprogesterone Steroids in Human Endometrial Cells (Abstract only) Publ: *Journal of Clinical Endocrinology Metabolism* Vol/Iss: 62 (6) pp.: 1116–1123 Date: Jun. 1986.

Author: Klauber et al. Title: Inhibition of Angiogenesis and Breast Cancer in Mice by the Microtubule Inhibitors 2–Methoxyestradiol and Taxol Publ: *Cancer Research* Vol/Iss: 57 pp.: 81–86 Date: Jan. 1, 1997.

Author: Lebras, J. et al. Title: Activation and Regioselective Ortho–Functionalization of the A–Ring of B–Estradiol Promoted by "Cp*Ir": An Efficient Organometallic Procedure for the Synthesis of 2–Methoxyestradiol Publ: *Organometallics* Vol/Iss: 16 pp.: 1765–1771 Date: 1997.

Author: Lin et al. Title: Interactions of Tubulin with Potent Natural and Synthetic Analogs of the Antimitotic Agent Combretastatin: A Structure–Activity Study Publ: *Molecular Pharmacology* Vol/Iss: 34 (2) pp.: 200–208 Date: Aug. 1988.

Author: Lincoln et al. Title: Conformation of Thiocolchicine and Two B–Ring–Modified Analogues Bound to Tubulin Studied with Optical Spectroscopy Publ: *Biochemistry* Vol/Iss: 30 (5) pp.: 1179–1187 Date: Feb. 5, 1991.

Author: Lottering et al. Title: Effects of the 17β–Estradiol Metabolites on Cell Cycle Events in MCF–7 Cells Publ: *Cancer Resarch* Vol/Iss: 52 pp.: 5926–5932 Date: Nov. 1, 1992.

Author: Lottering et al. Title: 17β–Estradiol Metabolites Affect Some Regulators of the MCF–7 Cell Cycle Publ: *Cancer Letters* Vol/Iss: 110 pp.: 181–186, Date: 1996.

Author: Mayol et al. Title: Ethynylestradiol–Induced Cell Proliferation in Rat Liver Involvement of Specific Populations of Hepatocytes (Abstract only) Publ: *Cacinogenesis,* Vol/Iss: 12 (12) pp.: 2381–2388 Date: 1992.

Author: Meikrantz et al. Title: Apoptosis and the Cell Cycle Publ: *Journal of Cellular Biochemistry* Vol/Iss: 58 pp.: 160–174 Date: Jun. 1995.

Author: Miller et al. Title: Synthesis of Structure–Activity Profiles of A–Homoestranes, the Estratropones Publ: *Jouronal of Medicinal Chemistry* Vol/Iss: 40 pp.: 3836–3841 Date: 1997.

Author: Morgan et al. Title: Calcium and Oestrogen Interactions upon the Rat Thymic Lymphocyte Plasma Membrane Publ: *Biochemical and Biophysical Research Communications* Vol/Iss: 72 (2) pp.: 663–672 Date: Sep. 20, 1976.

Author: Mukhopadhyay et al. Title: Induction of Apoptosis in Human Lung Cancer Cells after Wild–Type p53 Activation by Methoxyestradiol Publ: *Oncogene* Vol/Iss: 14 pp.: 379–384 Date: 1997.

Author: Mukundan et al. Title: Liver Regeneration in Oral Contraceptive Treated Female Rats—Effects of Moderate Malnutrition Publ: *Hormone and Metabolic Research* Vol/Iss: 16 pp.: 641–645 Date: Dec. 1984.

Author: Nakagawa–Yagi et al. Title: The Endogenous Estrogen Metabolite 2–Methoxyestradiol Induces Apoptotic Neuronal Cell Death In Vitro Publ: *Life Sciences* Vol/Iss: 58 (17) pp.: 1461–1467 Date: 1996.

Author: Nakamura et al. Title: Studies on the Total Synthesis of dl–Colchicine, I. Synthesis of 3–Hydroxy–9, 10, 11–trimethoxy–1,2,3,4,6,7–hexahydro–5H–dibenzo[a,c] cycloheptatrien–5–one Publ: *Chemical and Pharmaceutical Bulletin* Vol/Iss: 10 pp.: 281–290 Date: 1962.

Author: Nambara et al. Title: Studies on Steroid Conjugates. III. New Synthesis of 2–Methoxyestrogens Publ: *Chem. Pharm. Bulletin* Vol/Iss: 18 (3) pp.: 474–480 Date: Mar. 1970.

Author: Napolitano et al. Title: 11 Beta–Substituted Estradiol Derivatives. 2. Potential Carbon–11 and Iodine–Labeled Probes for the Estrogen Receptor (Abstract only) Publ: *Journal of Medical Chemistry* Vol/Iss: 38 (14) pp.: 2774–2779 Date: Jul. 7, 1995.

Author: Nishigaki et al. Title: Anti–Proliferative Effect of 2–Methoxyestradiol on Cultured Smooth Muscle Cells from Rabbit Aorta Publ: *Atherosclerosis* Vol/Iss: 113 pp.: 167–170 Date: 1995.

Author: Ochs et al. Title: Effect of Tumor Promoting Contraceptive Steroids on Growth and Drug Metabolizing Enzymes in Rat Liver (Abstract only) Publ: *Cancer Research* Vol/Iss: 46 (3) pp.: 1224–1232 Date: 1986.

Author: Oppolzer et al. Title: 177. The Enantioselective Synthesis of (+)-Estradiol from 1,3-Dihydrobenzo[c]thiophene-2,2-dioxide by Successive Thermal $SO_2$-Extrusion and Cycloaddition Reactions Publ: *Helvetica Chimica Acta* Vol/Iss: 63 pp.: 1703–1707 Date: 1980.

Author: Parthasarathy et al. Title: Antioxidant: A New Role for RU-486 and Related Compounds (Abstract only) Publ: *Journal of Clinical Investigation* Vol/Iss: 94 (5) pp.: 1990–1995 Date: Nov. 1994.

Author: Paull et al. Title: Indentification of Novel Antimitotic Agents Acting at the Tubulin Level by Computer-assisted Evaluation of Differential Cytotoxicity Data Publ: *Cancer Research* Vol/Iss: 52 pp.: 3892–3900 Date: Jul. 15, 1992.

Author: Poli et al. Title: Tumor Necrosis Factor α Functions in an Autocrine Manner in the Induction of Human Immunodeficiency Virus Expression Publ: *Proeedings of the National Academy of Science USA* Vol/Iss: 87 pp.: 782–785 Date: Jan. 1990.

Author: Ravindra, R., Title: Effect of Estradiol on the in vitro Assembly of Rat Brain Tubulin Publ: *Journal of Indian Institute of Science* Vol/Iss: 64 (3) pp.: 27–35 Date: Mar. 1983.

Author: Sakakibara et al. Title: Effects of Diethylstilbestrol and its Methl Ethers on Aneuploidy Induction and Microtubule Distribution in Chinese Hamster V79 cells Publ: *Mutation Research* Vol/Iss: 263 pp.: 269–276 Date: Aug. 1991.

Author: Sato et al. Title: Effect of Estradiol and Ethynylestradiol on Microtubule Distribution in Chinese Hamster V79 Cells Publ: *Chemical and Pharmaceutical Bulletin* Vol/Iss: 40 (1) pp.: 182–184 Date: Jan. 1992.

Author: Sato et al. Title: Disruptive Effect on Diethylstilbestrol on Microtubules Publ: *Gann* Vol/Iss: 75 pp.: 1046–1048 Date: Dec. 1984.

Author: Sawada et al. Title: Colchicine–Like Effect of Diethylstilbestrol (DES) on Mammalian Cells in Vitro Publ: *Mutation Research* Vol/Iss: 57 pp.: 175–182 Date: May 1978.

Author: Seegers et al. Title: Cyclic–AMP and Cyclic–GMP Prouction in MCF–7 Cells Exposed to Estradiol–17 Beta, Catecholestrogens and Methoxy–Estrogens in MCF–7 Cells (Meeting Abstract only) Publ: *Joint MCI–1st Symposoium. Third 1st International Symposium. Biology and Therapy of Breast Cancer* Date: Sep. 25, 1989.

Author: Seegers, J.C. et al. Title: The Cytotoxic Effects of Estradiol–17B, Catecholestradiols and Methoxyestradiols on Dividing MCF–7 and HeLa Cells Publ: *Journal of Steroid Biochemistry* Vol/Iss: 32 (6) pp.: 797–809 Date: 1989.

Author: Sharp et al. Title: Diethylstilbestrol: the Binding and Effects of Diethylstilboestrol upon the Polymerisation and Depolymerisation of Purified MIcrotubule Protein in vitro Publ: *Carcinogens* Vol/Iss: 6 (6) pp.: 865–871 Date: Jun. 1985.

Author: Spicer et al. Title: Catecholestrogens Inhibit Proliferation and DNA Synthesis of Procine Granulosa Cells in Vitro: Comparison with Estradiol, 5α–dihydrotestosterone, Gonadotropins and Catecholamines Publ: *Molecular and Cellular Endocrinology* Vol/Iss: 64 pp.: 119–126 Date: 1989.

Author: Sternlicht et al. Title: Colchicine Inhibition of Microtubule Assembly via Copolymer Formation Publ: *The Journal of Biological Chemistry* Vol/Iss: 254 (20) pp.: 10540–10550 Date: Oct. 25, 1979.

Author: Sun et al. Title: Antitumor Agents. 139. Synthesis and Biological Evaluation of Thiocolchicine Analogs 5,6–Dihydro–6(S)–(acyloxy)–and 5,6–Dihydro–6(S)–[(acyloxy)methyl}–1,2,3–Publ: *Journal of Medicinal Chemistry* Vol/Iss: 36 pp.: 544–551 Date: Mar. 5, 1993.

Author: Sunagawa et al. Title: Synthesis of Colchicine; Synthesis of dl–'Demethyoxydeoxy–hexahydrocolchicine Publ: *Chem. Pharm. Bulletin* Vol/Iss: 9 pp.: 81–83 Date: 1961.

Author: Teranishi, M. et al. Title: Methylation of Catechol Estrogen with Diazomethane Publ: *Chemical and Pharmaceutical Bulletin* Vol/Iss: 31 (9) pp.: 3309–3314 Date: Sep. 1993.

Author: Tishler et al. Title: Microtubule–Active Drugs Taxol, Vinblastine, and Nocodazole Increase the Levels of Transcriptionally Active p53 Publ: *Cancer Research* Vol/Iss: 55 pp.: 6021–6025 Date: Dec. 15, 1995.

Author: Tsutsui et al. Title: Comparison of Human Versus Syrian Hamster Cells in Culture for Induction of Mitotic Inhibition, Binucleation and Multinucleation, Following Treatment with Four Aneuploidogens Publ: *Toxicology in Vitro* Vol/Iss: 4 (1) pp.: 75–84 Date: 1990.

Author: Utne et al. Title: The Synthesis of 2–and 4–Fluoroestradiol Publ: *Journal of Organic Chemistry* Vol/Iss: 33 (6) pp.: 2469–2473 Date: Jun. 1968.

Author: Van Geerestein et al. Title: Structure of 11.beta.–(4–(dimethylamino)pentyl)–17.beta.–hydroxy–17.alpha.–(2–propenyl) estra–4,9–dien–3–one (Identifier only) Publ: *Acta Crystall Ogr., Sect. C: Cryst. Struct. Commun.* Vol/Iss: C43 (2) pp.: 319–322 Date: 1987.

Author: Van Tamelen et al. Title: The Synthesis of Colchicine Publ: *Tetrahedron* Vol/Iss: 14 pp.: 8–34 Date: Sep. 1961.

Author: Wang, Z. et al. Title: An Optimized Synthesis of 2–Methoxyestradiol, a Naturally Occurring Human Metabolite with Anticancer Activity Publ: *Synth. Commun.* Vol/Iss: 28 (23) pp.: 4431–4437 Date: 1998.

Author: Wheeler et al. Title: Mitotic Inibition and Aneuploidy Induction by Naturally Occurring and Synthetic Estrogens in Chinese Hamster Cells in Vitro Publ: *Mutation Research* Vol/Iss: 171 pp.: 31–41 Date: 1986.

Author: Wheeler et al. Title: Mitotic Inhibition and Chromosome Displacement Induced by Estradiol in Chinese Hamsters Cells Publ: *Cell Motility and the Cytoskeleton* Vol/Iss: 7 (3) pp.: 235–247 Date: 1987.

Author: Yue et al. Title: 2–Methoxyestradiol, an Endogenous Estrogen Metabolite, Induces Apoptosis in Endothelial Cells and Inhibits Angiogenesis: Possible Role for Stress–Activated Protein Kinase Signaling Pathway and Fas Expression Publ: *Molecular Pharmacology* Vol/Iss: 51 pp.: 951–952 Date: 1997.

Author: Numazawa et al. Title: Efficient Synthesis of 2–Methoxy–and 4–Methoxy–Estrogens Publ: *Journal of the Chemical Society* pp.: 533–534 Date: Jan. 1, 1983.

Author: Rao et al. Title: Structural Specificity of Estrogens in the Induction of Mitotic Chromatid Non–Disjunction in Hela Cells Publ: *Experimental Cell Research* Vol/Iss: 48 pp.: 71–81 Date: 1967.

Author: Rao et al. Title: A Novel, Two–Step Synthesis of 2–Methoxyestradiol Publ: *Synthesis,* pp.: 168–169 Date: Mar. 1, 1977.

Author: Sakakibara, Kyoichi, Title: 2–Hydroxy–1,3,5(10)–estratriene derivatives (abstract only) (Identifier: XP–002186126) Publ: *Chemical Abstracts* Vol/Iss: 60(1) Date: Jan. 6, 1964.

Author: Arnoldi et al. Title: Sweet Isovanillyl Derivatives: Synthesis and Structure–Taste Relationships of Conformationally Restricted Analogs (abstract only) Publ: *Journal of Agric. Food Chem.* Vol/Iss: 46(10) pp.: 4002–4010 Date: 1998.

Author: Audier et al. Title: Orientation de la fragmentation en spectrometrie de masse par introduction de groupements fonctionnels. VII.—Ethylenecetals de ceto–2 steroides Publ: *Bulletin De La Societe Chimique De France* Vol/Iss: 10 pp.: 3088–3090 Date: 1965.

Author: Cambie et al. Title: Aromatic Steroids. Part II. Chromium Trioxide Oxidation of Some Oestra–1,3,5(10)–trienes Publ: *Journal of the Chemical Society* Vol/Iss: 9 pp.: 1234–1240 Date: 1969.

Author: Fetizon et al. Title: Synthesis of 2–keto steroids (abstract only) Publ: *Bull. Soc. Chim. FR.* Vol/Iss: 8 pp.: 3301–3306 Date: 1968.

Author: Lichtenauer et al. Title: Zur Behandlung des Prostata–Karzinoms Publ: *Deutsches medizinishces Journal* Vol/Iss: 23 pp.: 248–249 Date: Jan. 1972.

Author: Limantsev et al. Title: Effect of some estrogen structural analogs on the development of the mouse embyo (abstract only) Publ: *Akush Jinekol.* Vol/Iss: 6 pp.: 55–56 Date: 1982.

Author: Miller, Thomas, Title: Tubulin as a Therapeutic Target (Abstract only) Publ: *Dissertations Abstracts International* Vol/Iss: 5907B pp.: 3454 Date: 1998.

* cited by examiner

USE OF ANTI-ESTROGENIC COMPOUNDS AS ANTI-FUNGAL AGENTS

The present application is a continuation of U.S. patent application Ser. No. 09/371,585, filed Aug. 10, 1999, now U.S. Pat. No. 6,239,123 B1 which claims the benefit of provisional application U.S. Ser. No. 60/096,145, filed Aug. 11, 1998.

FIELD OF THE INVENTION

This invention relates to the treatment of fungal infections with estrogenic derivatives.

BACKGROUND OF THE INVENTION

Candidiasis is a fungal infection of mucosal membranes and other tissues. The infection is caused by the yeast-like organism Candida. Numerous species of Candida exist, including C. albicans. The recent increase in candidiasis is most likely caused by the rising incidence of AIDS, more intensive regimens of cancer therapy, complications of abdominal or cardio-thoracic surgery, organ transplantations, burns and trauma. Immunocompromised individuals and women of childbearing age, especially pregnant women or women with one or more child births, are known to be more susceptible to microbial pathogenesis. Alteration of the fungi microenvironment is currently considered to be accountable for the initiation of C. albicans infection symptoms (1). Changes in pH, temperature, osmotic pressure, and hormonal concentrations are some of the environmental factors that induce virulence expression.

While most candidiasis patients are infected with C. albicans, the number of non-C. albicans infections has been growing steadily and may reflect the increased use of azole drug prophylaxis and therapy since some non-C. albicans species are innately resistant to these drugs. Additional risk factors commonly associated with the onset of candidiasis include protracted, broad-spectrum antibiotic therapies, invasive devices, and prolonged hospital stays. Under these conditions, an antibiotic resistant replacement flora, including one or more fungal species, can proliferate in the gastrointestinal tract and invade from mucosal foci to deep tissues, especially when mucosal integrity has been disrupted as a result of chemotherapy or surgery.

2-Methoxyestradiol (2ME2), an end product of 17β-estradiol metabolism, is a well-known anti-mitogen that suppresses the growth of rapidly dividing mammalian cells by interfering with the progression of their cell cycle. Although a number of studies have been published regarding the effects of 2ME2 and related derivatives on the proliferation of endothelial and tumor cells, nothing is known about the effects of this metabolite on the replication of non-mammalian cells.

Recently, 17β-estradiol has emerged as one of the agents that support C. albicans germination and growth (1, 2). Specifically, growth of yeast cells in serum stripped of any steroid compound (by means of activated charcoal) results in reduction of the percentage of germinating cells, and thus, in reduction in virulence. Supplementation of the stripped media with exogenous estradiol in nanomolar concentrations restores germination. This property is specific to 17β-estradiol, since cholesterol and the α-isomer of estradiol do not induce morphogenic changes in C. albicans. In addition, certain strains of C. albicans require the presence of 17α- or 17β-estradiol for rapid growth.

The importance of estrogen as a virulence factor is also reinforced by in vivo studies in which estrogen treatment is required to induce susceptibility of oophorectomized to vaginal colonization of C. albicans (3, 4), and the presence of an estrogen-binding protein (EBP) in C. albicans that binds to estrogen with high affinity and specificity (5, 6).

SUMMARY OF THE INVENTION

The present invention provides compounds that are useful for inhibiting the growth of fungi. The compounds are estrogenic derivatives, such as 2ME2, and analogs thereof. The compounds may be used for treating infections of fungi in humans and animals, or to prevent or inhibit the growth of fungi on any surface. Furthermore, the invention contemplates the use of anti-estrogenic compounds, such as tamoxifen and raloxifene, as anti-fungal treatments.

DETAILED DESCRIPTION OF THE INVENTION

Figure 1:
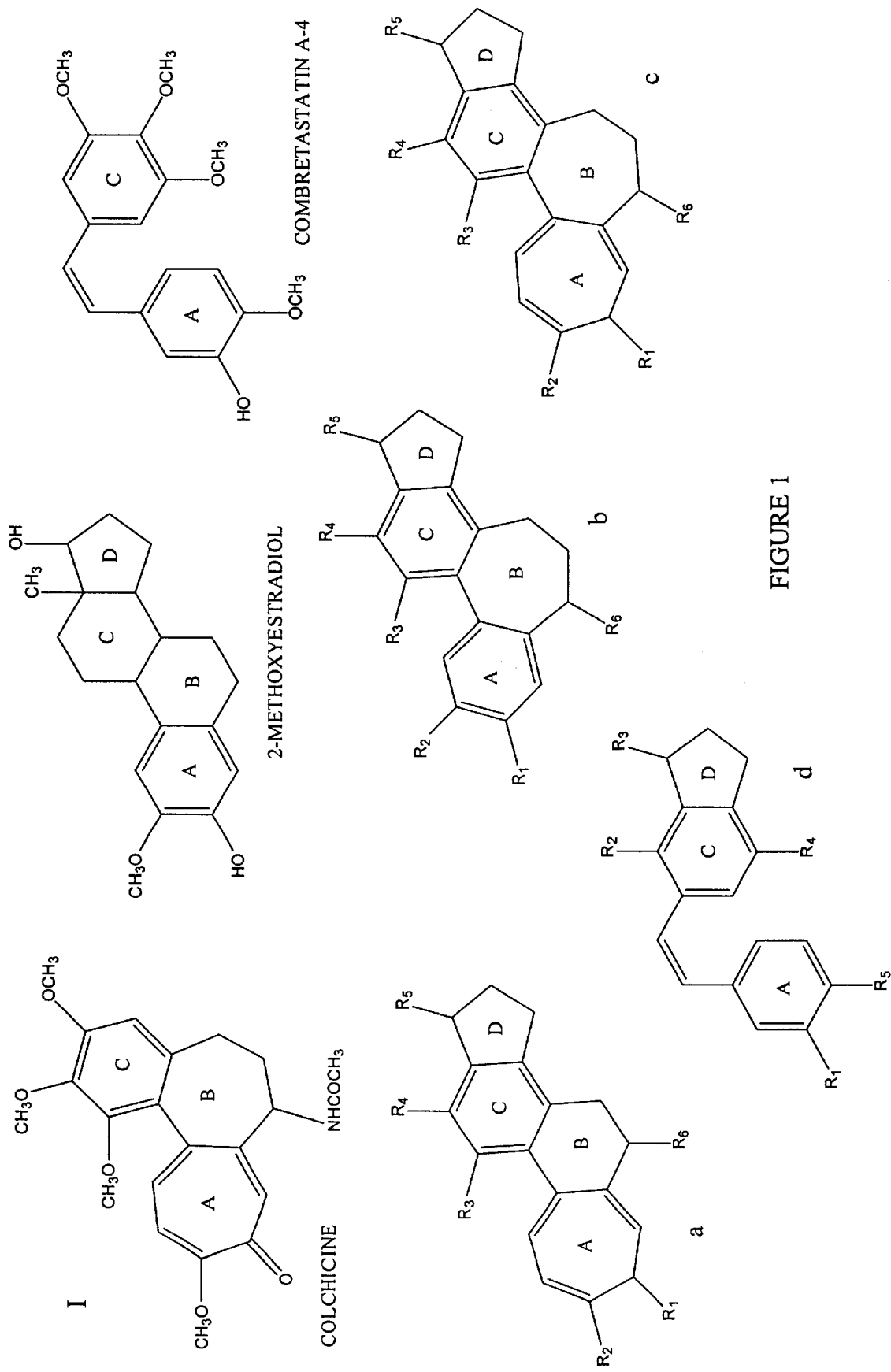
FIG. 1 shows the chemical structure of 2-methoxyestradiol, and the molecular formulae of colchicine, combretastatin A-4, and other estradiol derivatives.

As described below, compounds that are useful in accordance with the invention include estradiol derivatives that inhibit fungal growth, including the growth of yeasts and filamentous fungi. The present invention provides that estrogenic derivatives can be used as a fungi-static agent in humans and animals, as well as on any fungal-contaminated surface.

Specific compounds according to the invention are described below, such as 2-methoxyestradiol (2ME2), shown in FIG. 1. Those skilled in the art will appreciate that the invention extends to other derivatives of estrogens and estradiols, having the described characteristics. Examples of other estrogenic derivatives and analogs contemplated herein may be found in U.S. Pat. No. 5,661,143, which is incorporated by reference in its entirety. Given the present discovery that 2ME2 is a fungi-static agent, these characteristics can be determined for each estrogenic derivative and analog using the assays detailed below and known to those skilled in the art.

The invention provides that certain estrogenic derivatives, such as 2ME2, antagonize the stimulatory actions of other estrogens, such as 17β-estradiol, on the replication of yeast cells. The invention also provides for the use of anti-estrogenic compounds, such as tamoxifen and raloxifene, as anti-fungal treatments to inhibit the growth stimulatory effect of certain estrogens. Many other anti-estrogenic compounds are well-known in the aft.

Further, the invention provides that certain estrogenic derivatives, such as 2ME2, reverse resistance to common anti-fungal treatments. The administration of estrogenic derivatives, e.g. 2ME2, either alone or in combination with other anti-fungals, e.g. azoles, provides a new method for treatment of fungal infections, such as candidiasis.

Synthesis of Estrogenic Derivatives

The synthesis of the estrogenic derivatives described herein is well within the capability of one ordinarily skilled in the art. A specific description of the synthesis of the 2-ME derivatives and analogs contemplated herein can be found in Cushman, et al. Synthesis, antitubulin and antimitotic activity, and cytotoxicity of 2-methoxyestradiol, and endogenous mammalian metabolite of estradiol that inhibits tubulin polymerization by binding to the colchicine binding site, *J. Med. Chem.*, 38(12): 2042 (1995); and Cushman, et al. Synthesis of analogs of 2-methoxyestradiol with enhanced inhibitory effects on tubulin polymerization and cancer cell growth, *J. Med. Chem.* 40(15): 2323 (1997).

Known compounds that are used in accordance with the invention and precursors to novel compounds according to the invention can be purchased, e.g., from Sigma Chemical Co., St. Louis, Steroloids and Research Plus. Other compounds according to the invention can be synthesized according to known methods from publicly available precursors.

The chemical synthesis of estradiol has been described (Eder, V. et al., Ber 109, 2948 (1976); Oppolzer, D. A. and Roberts, D A. *Helv. Chim. Acta.* 63, 1703, (1980)). Synthetic methods for making seven-membered rings in multi-cyclic compounds are known (Nakamuru, T. et al. *Chem. Pharm. Bull.* 10, 281 (1962); Sunagawa, G. et al. *Chem. Pharm. Bull.* 9, 81 (1961); Van Tamelen, E. E. et al. *Tetrahedran* 14, 8–34 (1961); Evans, D. E. et al. *JACS* 103, 5813 (1981)). Those skilled in the art will appreciate that the chemical synthesis of estradiol can be modified to include 7-membered rings by making appropriate changes to the starting materials, so that ring closure yields seven-membered rings. Estradiol or estradiol derivatives can be modified to include appropriate chemical side groups according to the invention by known chemical methods (*The Merck Index*, 11th Ed., Merck & Co., Inc., Rahway, N.J. USA (1989), pp. 583–584).

FIG. 1 illustrates the molecular formulae of colchicine, 2-methoxyestradiol, combretastatin A-4, and other estradiol derivatives. Molecular formulae are drawn and oriented to emphasize structural similarities between the ring structures of colchicine, combretastatin A-4, estradiol, and certain estradiol derivatives. Estradiol derivatives can be made by incorporating colchicine or combretastatin A-4 structural motifs into the steroidal backbone of estradiol. FIG. 1, part I, depicts the chemical formulae of colchicine, 2-methoxyestradiol and combretastatin A-4. FIG. 1, part II a–d, illustrates estradiol derivatives that comprise structural motifs found in colchicine or combretastatin A-4. For example, part II a–c shows estradiol derivatives with an A and/or B ring expanded from six to seven carbons as found in colchicine and part IId depicts an estradiol derivative with a partial B ring as found in combretastatin A-4. Each C ring of an estradiol derivative, including those shown in FIG. 1, may be fully saturated as found in 2-methoxyestradiol. $R_{1-6}$ represent a subset of the substitution groups found in the claims. Each $R_1$–$R_6$ can independently be defined as —$R_1$, $OR_1$, —$OCOR_{11}$—$SR_1$, —F, —$NHR_2$, —Br, —I, or —C≡CH.

Particularly preferred estradiol derivatives, in addition to 2-methoxyestradiol, that have anti-fungal activity are among those represented by the formula:

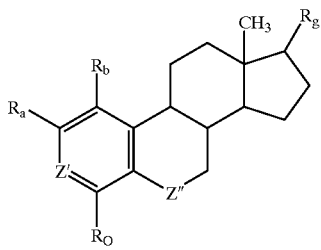

wherein:
a) $R_b$ and $R_o$ are independently —H, —Cl, —Br, —I, —F, —CN, lower alkyl, —OH, —$CH_2$—OH, —$NH_2$; or $N(R_6)(R_7)$, wherein $R_6$ and $R_7$ are independently hydrogen or an alkyl or branched alkyl with up to 6 carbons;

b) $R_a$ is —$N_3$, —C≡N, —$N_3$, —C≡C—R, —C=CH—R, —R—C=$CH_2$, —C≡CH, —O—R, —R—$R_1$, or —O—R—$R_1$ where R is a straight or branched alkyl with up to 10 carbons or aralkyl, and $R_1$ is —OH, —$NH_2$, —Cl, —Br, —I, —F or $CF_3$;

c) Z' is >CH, >COH, or >C—$R_2$—OH, where $R_2$ is an alkyl or branched alkyl with up to 10 carbons or aralkyl;

d) >C—$R_g$ is >$CH_2$, >C(H)—OH, >C=O, >C=N—OH, >C($R_3$)OH, >C=N—$OR_3$, >C(H)—$NH_2$, >C(H)—$NHR_3$, >C(H)—$NR_3R_4$, or >C(H)—C(O)—$R_3$, where each $R_3$ and $R_4$ is independently an alkyl or branched alkyl with up to 10 carbons or aralkyl; and e) Z" is >$CH_2$, >C=O, >C(H)—OH, >C=N—OH, >C=N—$OR_5$, >C(H)—C≡N, or >C(H)—$NR_5R_5$, wherein each $R_5$ is independently hydrogen, an alkyl or branched alkyl with up to 10 carbons or aralkyl.

Anti-Fungal Activity

Anti-fungal activity is evaluated by testing the ability of an estrogen derivative, or anti-estrogenic compound, to inhibit the growth of fungal species. A suitable assay is found in the following examples and in the literature. Using such an assay, an estrogenic derivative, or anti-estrogenic compound, is added to a fungal culture and observed for the ability to inhibit fungal growth after a time period. This result indicates that the estrogenic derivative, or anti-estrogenic compound, can inhibit fungal growth.

Indications

The invention can be used to treat any disease characterized by fungal infection. Such diseases include, but are not limited to candidiasis and thrush. The invention may also be used to prevent the growth of fungal species on inanimate objects, such as hospital equipment.

Administration

The compositions described above can be provided as physiologically acceptable formulations using known techniques, and these formulations can be administered by standard routes. In general, the combinations may be administered by the topical, oral, vaginal, rectal or parenteral (e.g., intravenous, subcutaneous or intramuscular) route. In addition, the combinations may be incorporated into biodegradable polymers allowing for sustained release, the polymers being implanted in the vicinity of where delivery is desired, for example, at the site of a tumor. The biodegradable polymers and their use are described in detail in Brem et al., *J. Neurosurg.* 74:441–446 (1991). The dosage of the composition will depend on the condition being treated, the particular derivative used, and other clinical factors such as weight and condition of the patient and the route of administration of the compound. However, for oral administration to humans, a dosage of 0.01 to 100 mg/kg/day, preferably 0.01–1 mg/kg/day, is generally sufficient.

The formulations include those suitable for oral, rectal, nasal, topical (including buccal and sublingual), vaginal or parenteral (including subcutaneous, intramuscular, intravenous, intradermal, intraocular, intratracheal, and epidural) administration. The formulations may conveniently be presented in unit dosage form and may be prepared by conventional pharmaceutical techniques. Such techniques include the step of bringing into association the active ingredient and the pharmaceutical carrier(s) or excipient(s). In general, the formulations are prepared by uniformly and intimately bringing into associate the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil emulsion and as a bolus, etc.

A tablet may be made by compression or molding, optionally with one or more accessory ingredients. Compressed tablets may be prepared by compressing, in a suitable machine, the active ingredient in a free-flowing form such as a powder or granules, optionally mixed with a binder, lubricant, inert diluent, preservative, surface-active or dispersing agent. Molded tables may be made by molding, in a suitable machine, a mixture of the powdered compound moistened with an inert liquid diluent. The tablets may optionally coated or scored and may be formulated so as to provide a slow or controlled release of the active ingredient therein.

Formulations suitable for topical administration in the mouth include lozenges comprising the ingredients in a flavored basis, usually sucrose and acacia or tragacanth; pastilles comprising the active ingredient in an inert basis such as gelatin and glycerin, or sucrose and acacia; and mouthwashes comprising the ingredient to be administered in a suitable liquid carrier.

Formulations suitable for topical administration to the skin may be presented as ointments, creams, gels and pastes comprising the ingredient to be administered in a pharmaceutical acceptable carrier. A preferred topical delivery system is a transdermal patch containing the ingredient to be administered.

Formulations for rectal administration may be presented as a suppository with a suitable base comprising, for example, cocoa butter or a salicylate.

Formulations suitable for nasal administration, wherein the carrier is a solid, include a coarse powder having a particle size, for example, in the range of 20 to 500 microns which is administered in the manner in which snuff is taken, i.e., by rapid inhalation through the nasal passage from a container of the powder held close up to the nose. Suitable formulations, wherein the carrier is a liquid, for administration, as for example, a nasal spray or as nasal drops, include aqueous or oily solutions of the active ingredient.

Formulations suitable for vaginal administration may be presented as pessaries, tampons, creams, gels, pastes, foams or spray formulations containing in addition to the active ingredient such as carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) conditions requiring only the addition of the sterile liquid carrier, for example, water for injections, immediately prior to use. Extemporaneous injection solutions and suspensions may be prepared from sterile powders, granules and tables of the kind previously described.

Preferred unit dosage formulations are those containing a daily dose or unit, daily sub-dose, as herein above recited, or an appropriate fraction thereof, of the administered ingredient.

It should be understood that in addition to the ingredients, particularly mentioned above, the formulations of this invention may include other agents convention in the art having regard to the type of formulation in question, for example, those suitable for oral administration may include flavoring agents.

The invention may be further appreciated by the following non-limiting examples, which are intended to be demonstrative of certain embodiments of the invention.

EXAMPLE 1

The ability of 3 $\mu$M 2ME2 to inhibit the growth of ten different strains of *C. albicans* was investigated. Nine of these strains were clinically isolated and maintained by interval of subculture with Sabouraouds dextrose agar and storage at 4° C.; the other strain was purchased from ATCC. Yeast cells were cultured with nitrogen broth devoid of mammalian steroid hormones in the presence and absence of 2ME2. At 5 and 12 hours after the addition of 2ME2, a small volume of control and treated cultures was drawn and plated on Sabouraouds dextrose agar plates. The plates were placed at 37° C. and the colonies counted 24 hours later. Table I illustrates that micromolar concentrations 2ME2 are able to suppress the growth of 9/10 strains of *C. albicans* tested here.

TABLE I

| Strain | Number of Control Colonies at 5 hrs | Number of Treated Colonies at 5 hrs | Number of Control Colonies at 12 hrs | Number of Treated Colonies at 12 hrs | Percentage of Inhibition at 12 hrs |
| --- | --- | --- | --- | --- | --- |
| ATCC | 17 | 15 | 221 | 67 | 70% |
| 1 | 15 | 16 | 254 | 50 | 57% |
| 2 | 61 | 51 | >400 | >400 | 0 |
| 3 | 16 | 14 | >400 | 86 | >78% |
| 4 | 13 | 17 | >400 | 113 | >72% |
| 5 | 34 | 14 | >400 | 85 | >79% |
| 6 | 51 | 32 | >400 | 131 | >67% |
| 7 | 22 | 13 | >400 | 148 | >63% |
| 8 | 23 | 14 | >400 | 98 | >75% |
| 9 | 21 | 15 | >400 | 90 | >77% |

EXAMPLE 2

The experiment described in Example 1 was repeated with 4 of the above strains and 3 newly isolated *C. albicans* strains. The following counts were taken from yeast cultures grown for 5 hours in the nitrogen base media in the presence and absence of micromolar concentrations 2ME2.

TABLE II

| Strain | Control Colonies | Treated Colonies | Percentage of Inhibition |
|---|---|---|---|
| 10 | 50 ± 2 | 51 ± 19 | 0% |
| 8 | 118 ± 12 | 59 ± 7 | 50% |
| 11 | 86 ± 6 | 74 ± 16 | 14% |
| ATCC | 64 ± 3 | 36 ± 6 | 44% |
| 2 | 88 ± 5 | 26 ± 7 | 70% |
| 12 | 155 | 77 ± 12 | 50% |
| 5 | 99 ± 7 | 58 ± 7 | 41% |

EXAMPLE 3

In a separate experiment, 1 nM 17β-estradiol was added to the cultures of *C. albicans* cells in the presence and absence of 1 μM 2ME2 and the number of colonies of yeast cells cultured for 5 hours with the above steroids were counted as previously described. Table III shows the data.

TABLE III

| Strain | Number of Colonies treated with estradiol | Number of Colonies treated with estradiol and $2ME_2$ | Percentage of Inhibition |
|---|---|---|---|
| 10 | 52 ± 2 | 23 ± 5 | 56% |
| 8 | 48 ± 7 | 25 ± 3 | 48% |
| 11 | 80 ± 1 | 55 ± 6 | 31% |
| ATCC | 63 ± 8 | 28 ± 12 | 55% |
| 2 | 58 ± 5 | 64 ± 2 | 0 |
| 12 | 120 | 56 ± 1 | 53% |
| 5 | 69 ± 13 | 39 ± 4 | 43% |

References

1. P. R. Gujjar, M. Finucane, and B. Larsen. The effect of Estradiol on Candida albicans Growth. Ann Clin Lab Sci, 27(2): 151–156 (1997).
2. S. White and B. Larsen. Candida albicans morphogenesis is influenced by estrogen. Cell Mol Life Sci, 53(9): 744–749 (1997).
3. B. Larsen and R. P. Galask. Influence of estrogen and normal flora on vaginal candidiasis in the rat. J. Reprod Med, 29: 863–868 (1984).
4. A. Cassone, F. De Bernadis, G. Santoni, D. Adriani, and M. Boccanera. Rats clearing a vaginal infection by Candida albicans acquire specific, antibody-mediated resistance to vaginal reinfection.
5. D. S. Loose, D. J. Schurman, and D. Feldman. A corticosteroid binding protein and endogenous ligand in Candida albicans indicating a possible steroid receptor system. Nature, 293: 477–479 (1981).
6. X. Zhao, D. Feldman, C. M. Ardies, and P. J. Malloy. Oestrogen-binding protein in Candida albicans: antibody development and cellular localization by electron immunohistrochemistry. Microbiology, 141: 2685–92 (1995).

All of the publications mentioned herein are hereby incorporated by reference in their entireties. The above examples are merely demonstrative of the present invention, and are not intended to limit the scope of the appended claims.

We claim:

1. A method of inhibiting the proliferation of a fungus in an individual, comprising administering to the individual a proliferation-inhibiting amount of an anti-estrogenic compound, wherein the anti-estrogenic compound is not tamoxifen.

2. The method of claim 1, wherein the anti-estrogenic compound is raloxifene.

3. The method of claim 1, wherein the fungus is Candida.

4. A method of treating a fungal infection in an individual, comprising administering to the individual a fungal infection-treatment effective amount of an anti-estrogenic compound wherein the anti-estrogenic compound is not tamoxifen.

5. The method of claim 4, wherein the anti-estrogenic compound is raloxifene.

6. The method of claim 4, wherein the fungal infection is candidiasis.

7. The method of claim 4, wherein the individual is a mammal.

8. The method of claim 4, wherein the individual is a human.

* * * * *